United States Patent
Kroner et al.

(12) 
(10) Patent No.: US 6,193,883 B1
(45) Date of Patent: *Feb. 27, 2001

(54) MICROFILTRATION APPARATUS

(75) Inventors: Karl-Heinz Kroner, Wolfenbüttel; Jens Vogel, Braunschweig, both of (DE)

(73) Assignee: Gesellscgaft fur Biotechnologische Forschung mbH (GRF), Braunchweig (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,308

(22) Filed: Jun. 30, 1997

(30) Foreign Application Priority Data

Jun. 28, 1996 (DE) ................................. 296 11 336

(51) Int. Cl.$^7$ ..................................................... B01D 65/08
(52) U.S. Cl. .................. 210/198.2; 210/321.63; 210/321.75; 210/413; 210/314; 210/317
(58) Field of Search ................ 210/321.63, 415, 210/413, 414, 321.75, 321.84, 198.2, 317, 266, 656, 314

(56) References Cited

U.S. PATENT DOCUMENTS 3,583,230 * 6/1971 Patterson ........................... 210/198.2
5,679,249 * 10/1997 Fendya et al. .................. 210/321.63

* cited by examiner

Primary Examiner—Matthew O. Savage
(74) Attorney, Agent, or Firm—Brooks & Kushman P.C.

(57) ABSTRACT

A filtration apparatus for separating and/or enriching dissolved substances from a suspension or suspensions having at least one filter means through which flow takes place, there being arranged on the retentate side of the filter means a means for producing a shear field which produces a virtually homogeneous shear field and pressure gradient across the inflow cross-section of the filter means. The means for producing the shear field may be formed by a rotationally symmetrical rotor. There may be used as filter means matrices that are suitable for the adsorption of the dissolved substances to be separated off. There come into consideration for that purpose surface-modified membranes, for example affinity membranes. The filter apparatus may be one-tier, two-tier or multi-tier.

5 Claims, 10 Drawing Sheets

MICROFILTRATION APPARATUS

The invention relates to an apparatus for the gentle continuous separation and purification of dissolved substances from suspensions, especially biologically active proteins from cell suspensions or from cultures, employing the principle of affinity filtration using surface-modified membranes.

Known processes for isolating and purifying proteins from cell suspensions frequently comprise a large number of steps which can be divided, in principle, into four subgroups: 1: cell separation and concentration; 2: pre-enrichment; 3: fine purification, and 4: polishing. In particular, steps 1 and 2 are critical with respect to product yield and product stability. Typical processes in those steps are centrifugation, microfiltration, ultrafiltration, precipitation and extraction.

Gentle continuous cell separation and enrichment of the target products is required especially in the preparation of biologically active proteins using animal cell cultures. Whilst the conventional tangential flow processes frequently used for that purpose, such as, for example, microfiltration and ultrafiltration, yield a particle-free filtrate, their performance in terms of flow, service life and product yield is limited on account of the known problems of membrane fouling, and further product treatment is required for the purpose of enrichment, such as, for example, chromatography. Other processes for cell separation, such as centrifugation, do not usually yield a particle-free supernatant, which in turn limits the subsequent chromatography steps.

From the point of view of economic viability and technical procedure, it is desirable to reduce the number of work-up steps. One approach comprises processes that combine the steps of cell separation, pre-enrichment and concentration. Three variants have been described to date, which are: a) the use of membrane affinity filtration, b) the use of fluidized/expanded processes, and c) the use of "big beads" in conventional column chromatography processes. In principle, those processes are capable of processing solids-carrying or cell-containing media, but only the membrane filtration process yields a particle-free filtrate and it is the only process suitable for continuous cell feedback.

Membrane affinity filtration has hitherto been used primarily for the treatment of particle-free solutions, such as, for example, for enriching pharmaceutical proteins from culture solutions (Brandt, S., Goffe, R. A., Kessler, S. B., O'Connor, J. L., Zale, S. E.: "Membrane-Based Affinity Technology for Commercial Scale Purifications", Bio/Technology 6, 779–782 (1988)). Typically, the membrane modules used are conventional tangential flow systems, such as, for example, hollow fibres, or filter stacks, which are used for direct filtration or membrane chromatography (Langlotz, P., Krause, S., Kroner, K. H.: "Affinitätsmembranen für die Bioproduktaufarbeitung", F&S Filtrieren u. Separieren, 5 (2) 62–70 (1991) and Thömmes, J., Kula, M. R.: "Membrane Chromatography—An Integrated Concept in the Downstream Processing of Proteins", Biotechnol. Progress, 11, 357–367 (1995)). The treatment of particle-containing suspensions has hitherto been described only in terms of an initial approach (Kroner, K. H.: "Cross-Flow Application of Affinity Membranes", Membrane Processes in Separation and Purification, NATO ASI Series E, Applied Sciences, Vol. 272, Kluwer Academic Publishers, Dordrecht (1994)).

A particular problem of the membrane process is membrane fouling, that is to say blockage or formation of a deposit on the membrane, as a result of which the performance and especially also the separation-specific properties, such as the separation limit—and in the case of affinity membranes also the adsorption characteristics—are adversely affected (Langlotz, P., Krause, S., Kroner, K. H.: "Affinitätsmembranen für die Bioproduktaufarbeitung", F&S Filtrieren u. Separieren, 5 (2) 62–70 (1991) and Kroner, K. H.: "Cross-Flow Application of Affinity Membranes", Membrane Processes in Separation and Purification, NATO ASI Series E, Applied Sciences, Vol. 272, Kluwer Academic Publishers, Dordrecht (1994)). In order to reduce those problems, it is customary to operate the membrane modules at very high tangential cross-flow speeds, preferably in the turbulent flow region. However, that results in a high longitudinal pressure loss, which in turn results in a non-uniform distribution of the flow across the membrane. That leads to a reduction in the membrane capacity, also known by the term "premature breakthrough", and in a broadening of the peak (Kroner, K. H.: "Cross-Flow Application of Affinity Membranes", Membrane Processes in Separation and Purification, NATO ASI Series E, Applied Sciences, Vol. 272, Kluwer Academic Publishers, Dordrecht (1994)). The use of conventional tangential flow systems for membrane affinity filtration in chromatography-analogous operation is therefore possible only to a limited degree. A further problem of conventional tangential flow systems is the occurrence of high shear forces, which can result in cell destruction especially when such modules are used in the filtration of animal cell cultures. A consequence of this is the release of cell content substances and cell fragments, which limit the performance of the membrane filtration further and severely restrict its use in continuous cell feedback.

Also known are rotary modules, such as, for example, rotating disk filters, in which the shear at the membrane is produced mechanically. That is described, for example, in Murkes, J. et al.: "Crossflow Filtration", Wiley, N.Y. (1988). Whilst those modules demonstrate higher filtration performances than tangential flow systems, the effective shear forces are, however, also higher and are distributed over the filter means non-uniformly as a function of the radius: their use with sensitive cells is therefore severely restricted.

The problem underlying the invention is accordingly to provide a filtration apparatus for the integrated separation and enrichment of dissolved substances from particle-containing suspensions, which apparatus achieves virtually optimum utilisation of the filter area combined with gentle treatment of the cell material and is capable of being scaled-up in simple manner.

The problem is solved by the features of claim 1. Advantageous arrangements of the invention are the subject matter of the subsidiary claims.

The present invention relates to an apparatus for separating and/or enriching dissolved substances from a suspension, having at least one filter means through which flow takes place, there being arranged on the retentate side of the filter means a means for producing a shear field which produces a virtually homogeneous shear field across the entire inflow cross-section of the filter means.

Preferably, the means for producing a shear field is formed by a rotationally symmetrical rotor, the distance between the rotor and the filter means preferably increasing radially outwards in order to compensate for the increased circumferential speed, the homogeneous shear field thus being produced. A preferred construction of the rotationally symmetrical rotor is the simple conical rotor in which the distance (gap width) s is a linear function of the radius r. It is, of course, sufficient for the rotor to exhibit that linear dependency only in the region of the filter membrane, that is to say the cone may also be a truncated cone. The filter membrane is usually planar and the filter can be operated, depending on the use, as a cross-flow filter.

Preferably, the ratio of the gap width s between the filter membrane and the rotor to the rotor radius r is less than 0.2, that is to say s/r <0.2; preferably s/r <0.1 and >0.05. The cone angle φ is in the region of <16°, preferably from 3 to 6°. Preferably, the cone angle φ of the rotor cone is approximately 4°.

It is also possible for the retentate or concentrate to be discharged through an outlet opening arranged near the axle, or through the axle itself if the axle is in the form of a hollow shaft.

In order to increase the total filter area and thus to increase the filtering performance of the filtering apparatus, it is also possible for the surface of the rotor cone or rotor truncated cone to be constructed in the form of a filter, for example by providing the surface with an appropriate porosity. In that case, the shear field produced acts upon both surfaces, that is to say the planar surface of the filter itself and the conical surface that is in the form of a filter. The filtrate produced in the rotor, which in the case in question is hollow, can be removed, for example, by way of the above-mentioned hollow shaft. The active filter area available can thus advantageously be enlarged without the apparatus itself having to be enlarged, the advantages of the shear field being retained.

The filtration apparatuses according to the invention can be used to form filtration systems by connecting them in series, in other words in a stack arrangement, or in parallel. In other words, the performance of the filtration system can be adapted to requirements.

As filter means there are preferably used surface-modified membranes, especially affinity membranes based on microfiltration membranes. Such membranes may be single layers, or stacks of multiple layers to increase the total capacity, or combinations (sandwiches) of surface separating membranes and active packing material (gels, fibres, papers, or the like). With that apparatus it is possible to achieve chromatography-analogous operation with particle-containing suspensions.

The special advantages of the apparatus according to the invention are given hereinafter:

The described filtration system permits a high filtrate flow combined with gentle treatment of the cell material, owing to the special hydrodynamics. In contrast to known rotary disk filters, when a conical rotor is used a shear gradient that is virtually uniform and is independent of the radius is produced over the entire membrane cross-section. It may therefore be assumed that the cells are kept away from the membrane wall (the site of highest wall shear stress) by virtue of the so-called "hydrodynamic lift effect" (Vasseur, P., Cox, R. G.: "The Lateral Migration of a Spherical Particle in Two-Dimensional Shear Flow", J. Fluid Mech. 78, 385–401 (1976)) and are to be found predominantly in the region of the core flow where there are low shear rates by virtue of the parabolic profile of the velocity gradient. That behaviour can be used especially advantageously in the filtration of animal cells ($r_p$>3 μm). Calculations show that filtrate flow rates of >100 l/hm² are attainable for more than 90% of the membrane surface area (where A=f[$r^2$]). Conventional filtration systems under identical conditions typically exhibit filtration performances of <<100 l/hm².

In contrast to conventional rotary disk filters (high-shear filters), which are usually operated in the turbulent flow region IV (Murkes, J., Carlsson, C. G.: "Crossflow Filtration", Wiley, N.Y. (1988)), the present filtration apparatus can be operated in the laminar flow region II (Murkes, J., Carlsson, C. G.: "Crossflow Filtration", Wiley, N.Y. (1988)), which positively assists the "hydrodynamic lift effect" mentioned under point 1.

In contrast to conventional tangential flow filters, which demonstrate a large flow-dependent drop in pressure over the length of the membrane channel (P=f[w,L,Re]), the radius-dependent centrifugal pressure gradient (P=[$w^2$]; w=ω* r) in the present system is small and is not dependent upon the viscosity of the medium. A comparison of the length-dependent or radius-dependent pressure and flow profiles of a conventional tangential flow module (hollow fibre module) and of the filtration module according to the invention having radial shear shows that, for the hollow fibre module, under the typical operating conditions presented (w=2 m/s, TMP=0.1 bar) there is a loss of pressure of 0.2 bar under laminar conditions and of 0.96 bar under turbulent conditions and, for the module according to the invention, there is a nominal centrifugal loss of pressure of only 40 mbar. Surprisingly, measurements have shown that only approximately ¹⁄₁₀ of that pressure difference is active at the membrane, which is probably owing to an internal return flow between the rotor and stator. As a result, for the rotary module according to the invention, there is a virtually constant pressure gradient over the entire membrane and thus a uniform flow over the entire inflow cross-section of the filter means. Accordingly, there is better residence time behaviour for the flow through the filter means and—as a result—a significant increase in the utilisation of the membrane capacity (>90%) in chromatography-analogous operation. In contrast to tangential flow modules, the apparatus according to the invention accordingly allows virtually optimum chromatography-analogous operation.

In contrast to other separating systems, the use of the apparatus according to the invention yields a completely particle-free filtrate which can be fed to further purification steps without difficulty and without further treatment. In contrast to the "fluidized bed" and "big beads" processes, the apparatus according to the invention allows operation with continuous cell feedback, as in, for example, perfusion processes with animal cell cultures. In contrast to tangential flow modules and other known rotary disk filters, the apparatus according to the invention allows efficient and gentle cell separation whilst retaining the cell vitality, especially also of sensitive cell cultures.

The scaling-up of the apparatus according to the invention can be effected in simple manner as follows:

a) The use of more than one filter layer to increase the capacity; for that purpose there may be used membrane stacks or stacks of filter means (analogously to column packing in chromatography);

b) The use of more than one filter layer by the multi-tier arrangement according to the rotor/stator principle; for example, in that arrangement one rotary element is bounded by two filter means;

c) An increase in the radius of the filter cell; in that arrangement, with constant circumferential speed (w=const.=ω* r), the radial pressure gradient is independent of length, that is to say it is identical for filters having different diameters, in contrast to tangential flow modules in which, at constant cross-flow speed, the pressure loss increases with the length.

Preferred embodiments of the invention are described with reference to the accompanying drawings, in which.

Figure 1A:
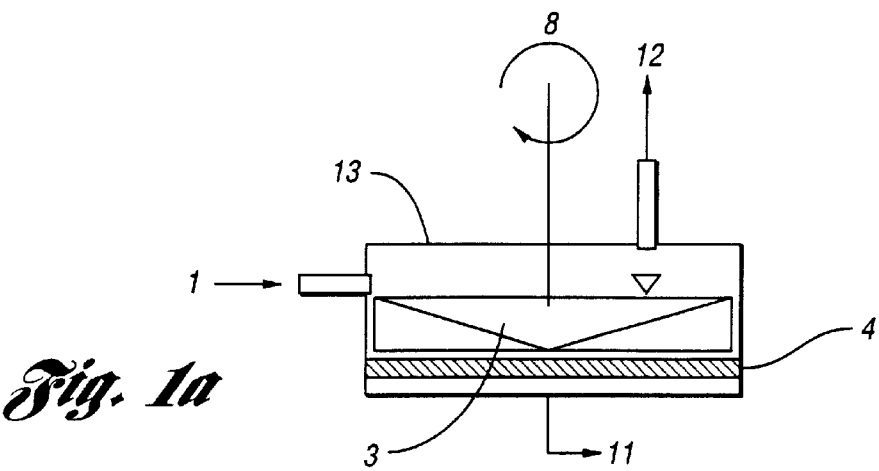
FIG. 1 shows the general structure and the operating principle of a one-tier (a), a two-tier (b) and a multi-tier (c) apparatus according to the invention.
Figure 1B:
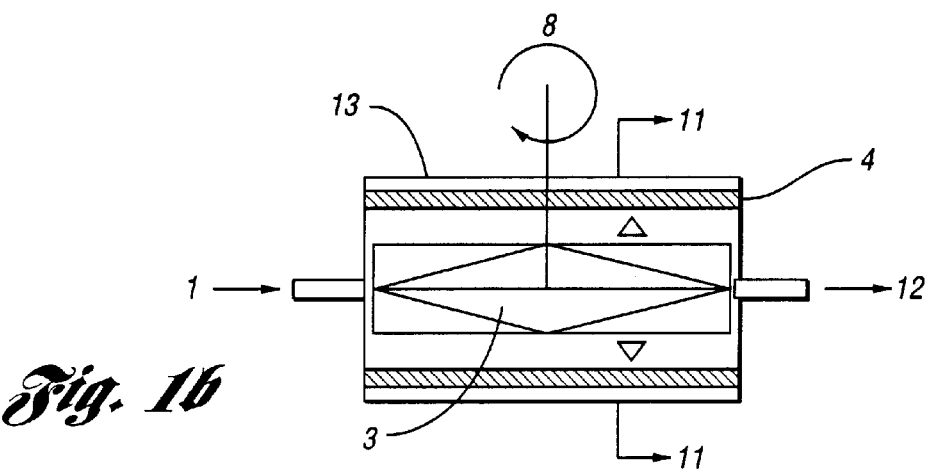
Figure 1C:
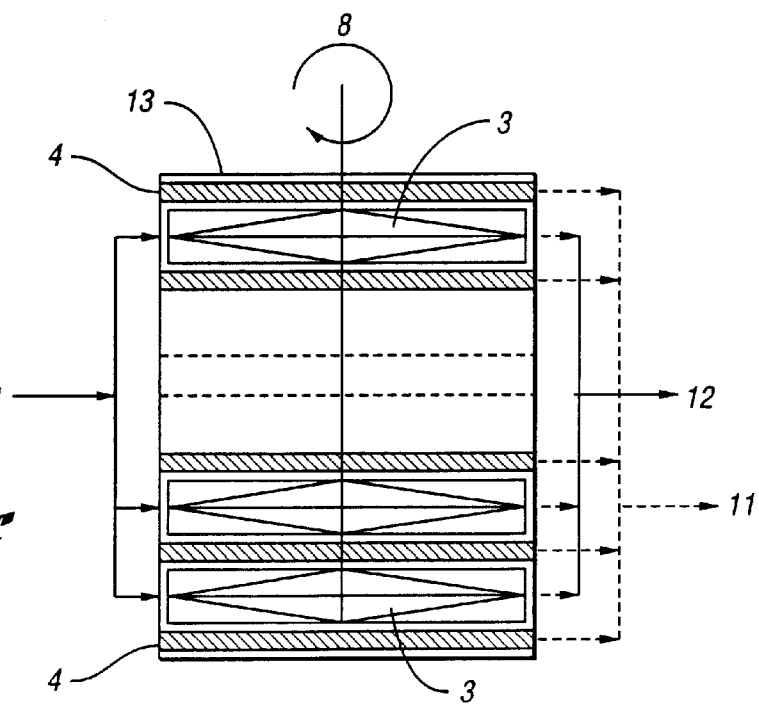

FIG. 1 shows a means 3, arranged in a preferably cylindrical housing 13, for producing a homogeneous shear field, there preferably being arranged opposite to a filter means 4 a rotationally symmetrical rotor 3, especially a conical rotor 3, which ensures a uniform flow over the filter means 4 to prevent the formation of a deposit on the filter means 4. The rotor 3 is rotated about its axis of symmetry 8. The suspension to be filtered is fed into the module above the filter means 4 at point 1 by means of a suitable external device, for example a pump, and leaves the module by way of the retentate outlet 12. By application of an external pressure, a uniform filtrate flow is produced across the filter means and is discharged by way of the filtrate outlet 11. The operating parameters of pressure, shear (speed of rotation) and supply of suspension may be selected as desired. The filter means 4 may be any filter layer, preferably a membrane, that ensures complete retention of particles, or may be a surface-modified membrane that can be used simultaneously for the adsorption of the target product. The simplest embodiment is a one-tier arrangement having a rotor 3 and a filter means 4 (a). In order to increase the filter area and to utilise the entire rotor chamber, filter means 4 may be inserted both above and below the rotor 3, the rotor 3 being of the same shape on both sides—two-tier embodiment (b). To increase the filter area further, it is possible, based on the two-tier arrangement, to construct a multiplier arrangement according to the rotor/stator principle (c). In that case, each rotor chamber element is bounded by two filter means 4. The triangles in FIG. 1 show the direction of flow. The same applies to FIGS. 2 and 3.

Figure 2A:
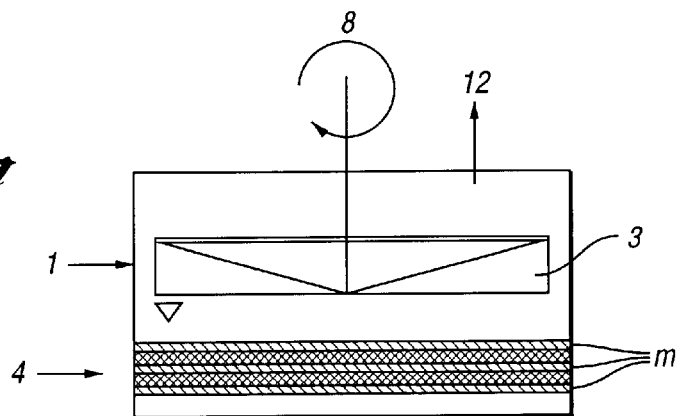
FIG. 2 shows the apparatus according to the invention in association with various alternative filter means, namely a multi-layer structure stack (a), a multi-layer structure sandwich (b) and a filter column (c)
Figure 2B:
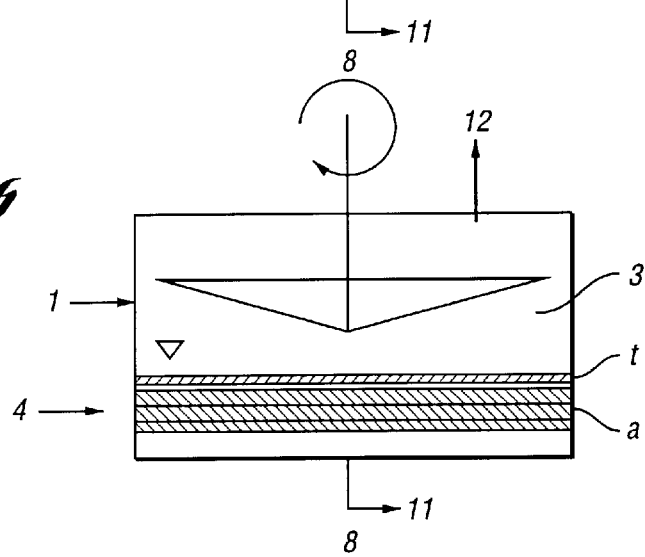
Figure 2C:
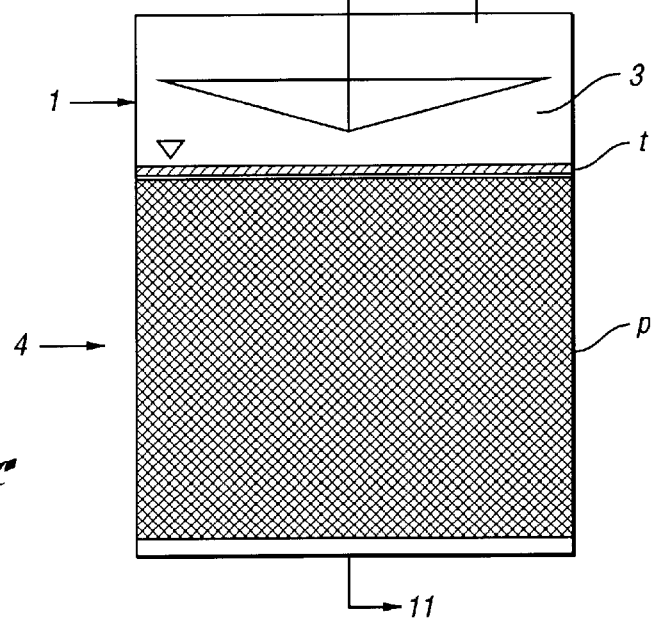

FIG. 2 shows the use of alternative filter means 4 in the apparatus according to the invention. In addition to the single-layer configuration, for example filter membrane, a multi-layer structure may be selected to increase capacity, for example a stack or packet of a plurality of membranes, the number of which n=i, especially bi-functional membranes, such as affinity membranes (a). A configuration comprising a combination of a separating layer or separating membrane t (for example, a micro-filter membrane) and one or more downstream active layers a may also be selected (b). In a special arrangement of that variant, the active layer may also be a packing or a bed P, consisting of a chromatography material, in which case the packing P is covered by a separating layer/membrane t. In principle, that arrangement constitutes a chromatography column with an integrated filter system (c).

Figure 3A:
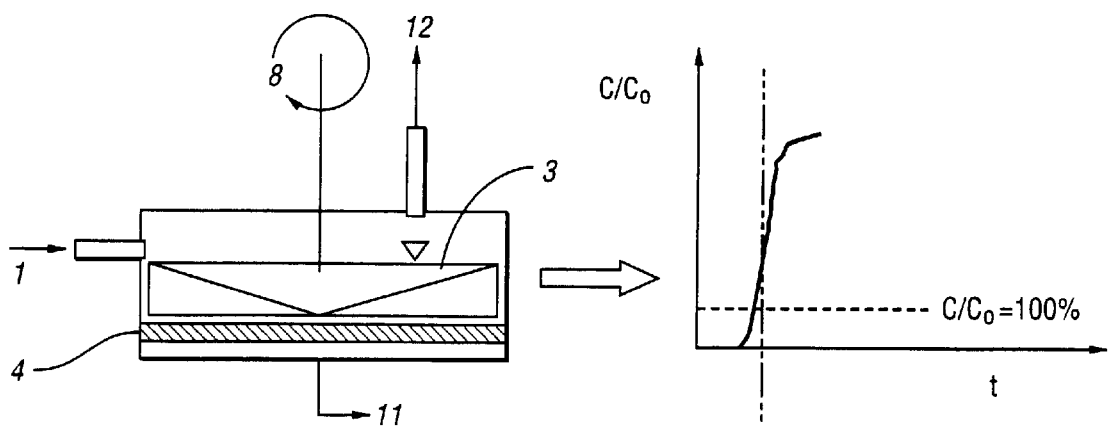
FIG. 3 illustrates the principle of operation of the apparatus for separating and enriching dissolved substances from particle-containing suspensions in chromatography-analogous operation comprising the steps a) charging, b) washing and c) eluting.
Figure 3B:
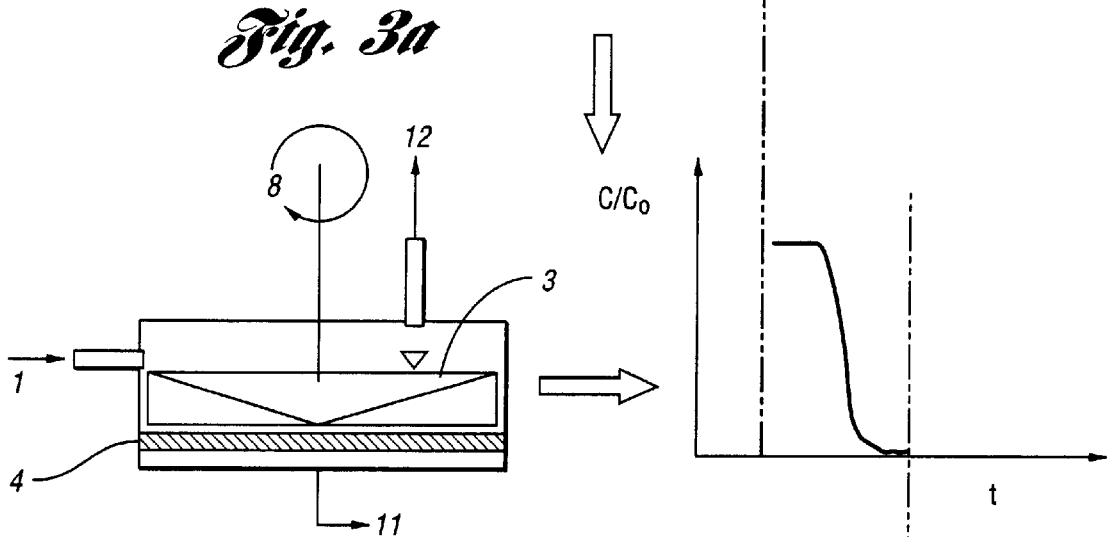
Figure 3C:
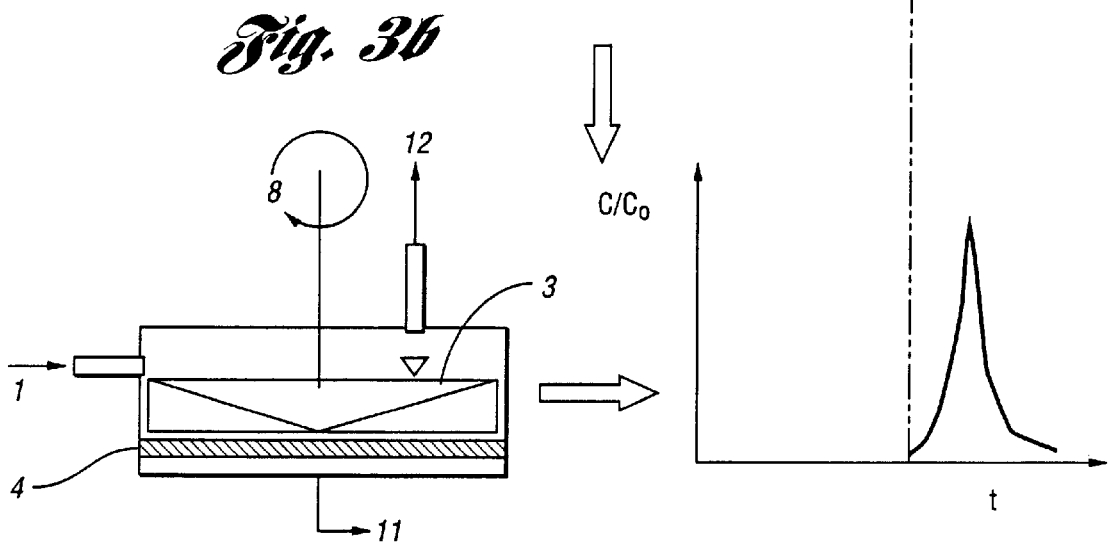

FIG. 3 illustrates the principle of operation of the filter apparatus, consisting of an inlet 1, a rotor 3 that is rotatable about an axle 8, a filter means 4 and a filtrate outlet 11 and a retentate outlet 12, in chromatography-analogous operation. Also shown is the curve of the filtrate concentration over time normalized relative to the initial concentration. The procedure is as follows: a) charging: the particle-containing suspension is fed through the module by means of an external pump and, if required, returned to the suspension vessel (for example, fermenter). With application of a specific filtration pressure, a particle-free filtrate flow is produced across the active filter layer. That filtrate flow is maintained until a product breakthrough can be observed in the filtrate. A typical approximate value is a maximum of approximately 10% of the initial concentration, that is to say $C/C_o=10\%$. Monitoring can be effected by means of a suitable analytical method, for example by photometry; b) washing: the supply of suspension is turned off and a suitable rinsing solution, for example a buffer, is fed through the module, with ongoing filtration, until the signal height in the filtrate approaches zero; c) elution: for the elution of the substances bound to the active layer, a suitable eluant, for example a buffer, is fed into the module in such a manner that initially the rinsing solution is displaced through the retentate outlet and then, after that outlet has been closed, the eluant is fed directly through the filter means, it being possible for elution to be carried out in steps or gradients, in a manner similar to that in chromatography. The eluted product may be collected or fractionated in known manner. Once the entire cycle has been completed, optionally after further rinsing with an equilibrating buffer, the module is switched to supply of suspension again for the next cycle.

Figure 4:
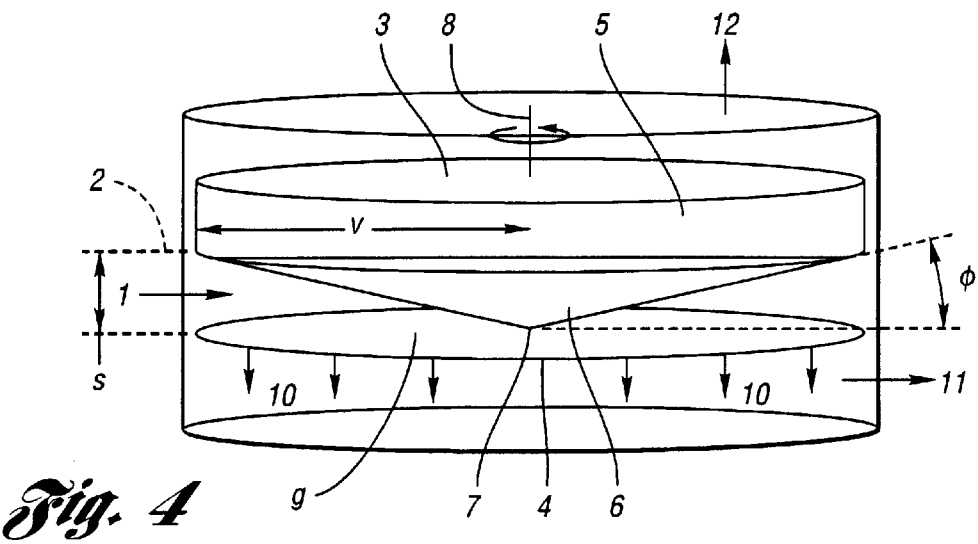
FIG. 4 is a diagrammatic perspective view of a one-tier filtration apparatus.

FIG. 4 is a perspective, diagrammatic view of a preferred arrangement of the filtration apparatus according to the invention. A supply flow 1 of the liquid or suspension to be filtered enters into the gap 2 having the gap width s, the gap 2 being defined by a rotor 3 and a filter means 4. The filter means 4 is formed by a planar filter membrane. The rotor 3 consists of a cylindrical body 5 and a conical section 6, the tip 7 of which points towards the filter membrane 4. The rotor 3 rotates about its axis of symmetry 8. As a result of that rotation, by virtue of the conical section 6 of the rotor 3, a constant shear gradient is produced over the entire filter surface 9 of the filter means 4. The resulting homogeneous shear field over the filter surface 9 is a function of the included angle between the cone 6 and the filter surface 9, of the distance $s_0$ of the cone tip from the filter surface 9, of the gap width s formed by the distance between the filter surface 9 and the cylindrical body 5, and also of the ratio of the gap width to the cone radius s/r. In a preferred arrangement, the rotor radius is from 35 to 150 mm, the distance of the tip of the cone from the membrane $s_0$ is variable and is from 0 to 5 mm, preferably 1 mm, and the cone angle φ of the rotor is from 3° to 6°, preferably 4°. Also, the ratio of the gap width s to the rotor radius r (s/r) is less than 0.1 and greater than 0.05. In the preferred arrangement, the liquid passes in an axial direction of flow 10 through the filter means 4 and is removed in the form of a filtrate 11 transversely to the through-flow direction 10. The retained retentate 12 flows in perpendicular direction away from the filter surface 9. There come into consideration as membranes for the filter means 4 commercially available filter membranes and also functional membranes, such as, for example, affinity membranes. The size of the rotor 3 and of the filter surface 9 depend upon the intended use and also upon the flow rate to be achieved, that is to say the filter performance to be achieved. For example, in order to increase the filter performance, such filters may be arranged in a system in parallel or in series in the form of a stack. Moreover, the filtration apparatus according to the invention does not have to be in the form of a cross-flow filter; it is also possible to convey the solution to be filtered to the filtration means 4 in the axial direction 10 of the axis of symmetry 8. In that case, the retentate 12 would then be removed transversely to the direction of supply. The drive of the rotor 3 is selected according to the proposed use. For example, the rotor may be driven directly by means of an electromotor or may be in the form of a magnetodynamic stirrer.

Figure 5A:
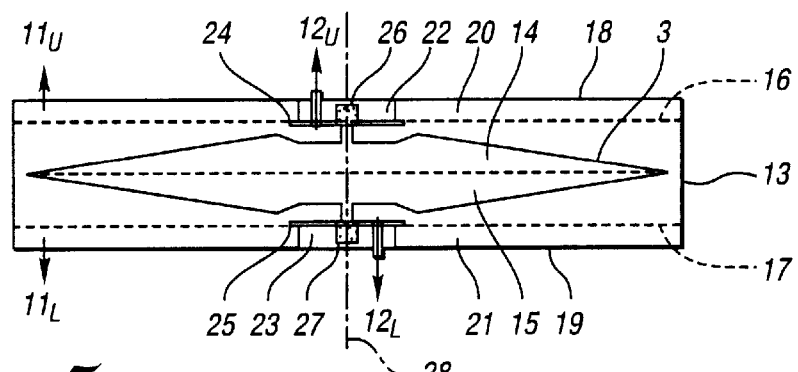
FIGS. 5A and 5B are a diagrammatic cross-section and a plan view, respectively, of a two-tier cross-flow filtration apparatus.

FIG. 5A shows a double-membrane stirring cell having a housing 13, in which there is arranged a rotor 3. The rotor 3 consists of an upper and a lower conical section 14, 15 in such a manner that a double cone directed outwardly on both sides is formed. On both sides of the rotor 3 that is in the form of a double cone, filter means 16, 17 are arranged in the housing 13 in such a manner that a space 20, 21 remains between the corresponding lower and upper cover wall 18, 19 of the housing 13 for receiving the filtrate $11_u$ and $11_l$, respectively. An upper and lower support 22 and 23 project axially symmetrically into the space formed by the housing 13, each of the supports 22, 23 having a corresponding cover 24, 25. There is provided in each cover a bearing 26 and 27 for receiving axially the axle 28 of the rotor 3. In the region of the bearing supports 22, 23, the rotor 3 is no longer of conical shape but is appropriately flattened off since no shear field has to be produced there on a membrane 16, 17. In other words, the cone 14, 15 is essentially in the form of a truncated cone since no shear field has to be produced in the region of the inwardly projecting supports 22, 23 because no filter membrane is present there. Moreover, in each cover 24, 25 of the corresponding support 22, 23, there is provided at least one retentate outlet $12_u$ and $12_l$, respectively, offset laterally to the side of the axis of symmetry.

Figure 5B:
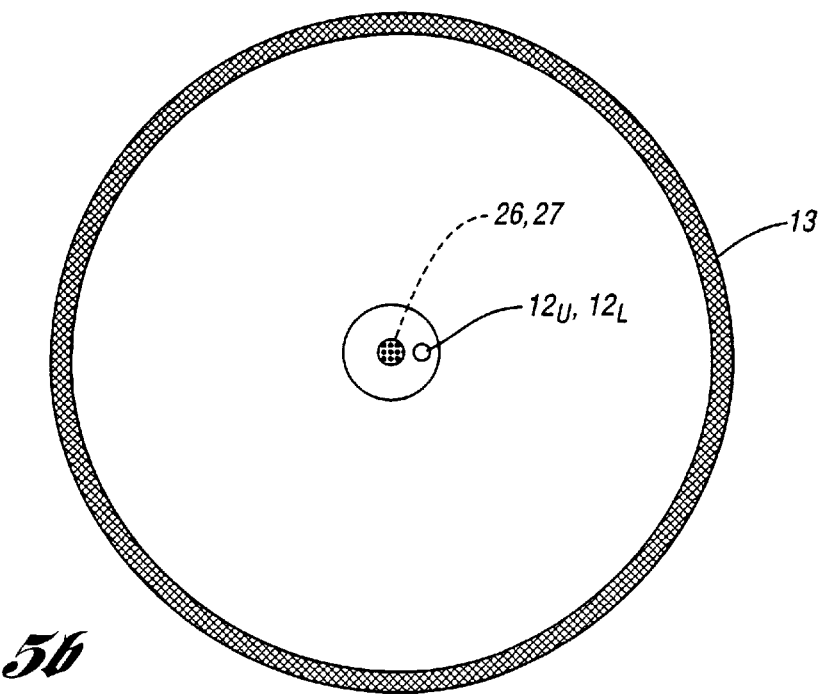

FIG. 5B is a plan view of the double-membrane stirring cell, which comprises the outer wall of the cylindrical housing 13. Arranged axially symmetrically therewith are the supports 22 and 23 having the axial bearings 26 and 27 and the retentate outlets $12_u$ and $12_l$, respectively. In that arrangement, the supply 1 of the solution or suspension to be clarified is effected in the tangential direction, for example through an appropriately formed feed pipe (not shown).

Figure 6:
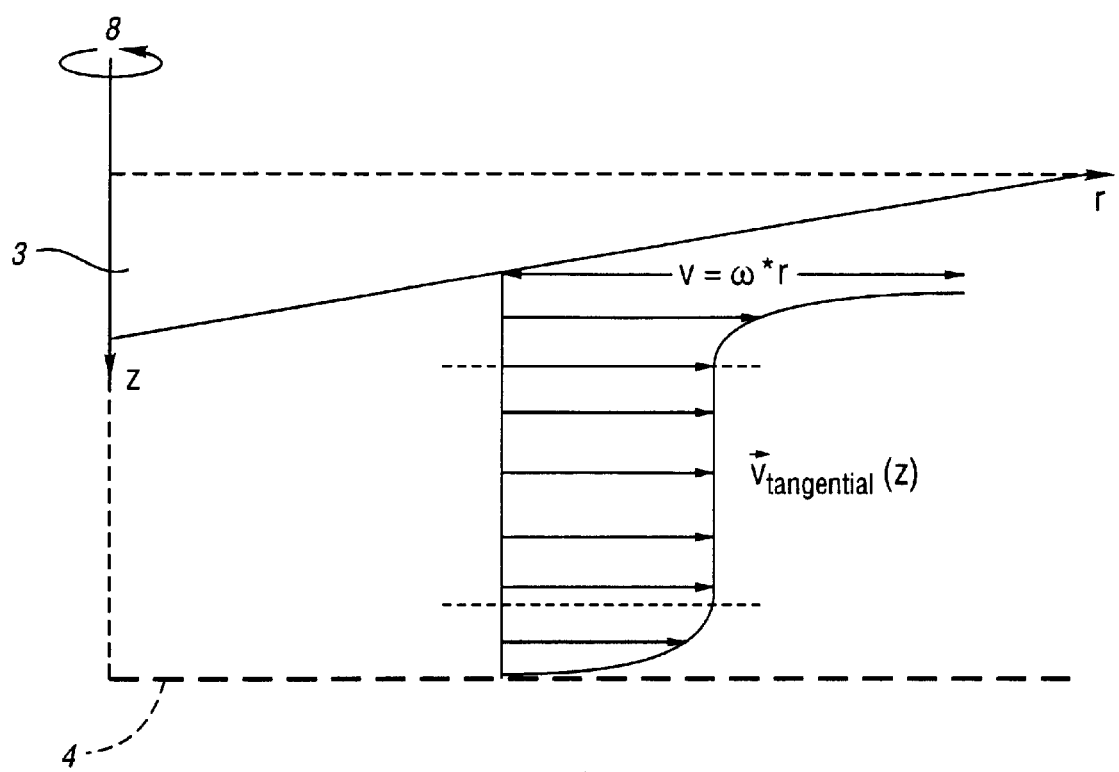
FIG. 6 is a diagrammatic representation of the velocity curve in the gap between the rotor and the filter means.

FIG. 6 is a diagrammatic representation of the postulated tangential velocity curve at the membrane in the gap between the rotor and stator (w=ω* r, z=axial direction) having a hyperbolic curve: velocity gradient at the wall>velocity gradient in the centre.

Figure 7:
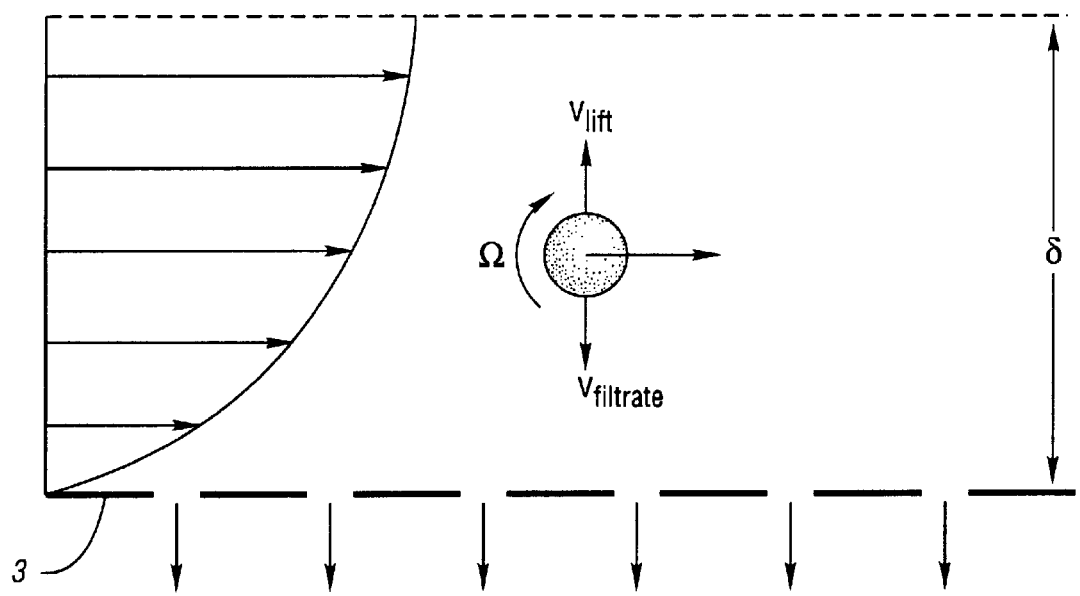
FIG. 7 is a diagrammatic representation of the lift effect.

FIG. 7 is a representation of the "lift force" effect on a spherical particle in a cross-flow parallel to a wall (membrane); Ω=rotation of the particle, triggered by the differences in velocity in the particle flow, δ=distance from the wall, $v_{lift}$=equivalent volumetric upward velocity (lift) of the particle, $v_{filtrate}$=equivalent volumetric downward velocity of the particle. In the state of equilibrium, $v_{lift}/v_{filtrate}=1$, that is to say the upward flow is equal to the filtrate flow and the particle adopts a constant position in the perpendicular direction relative to the membrane.

Figure 8:
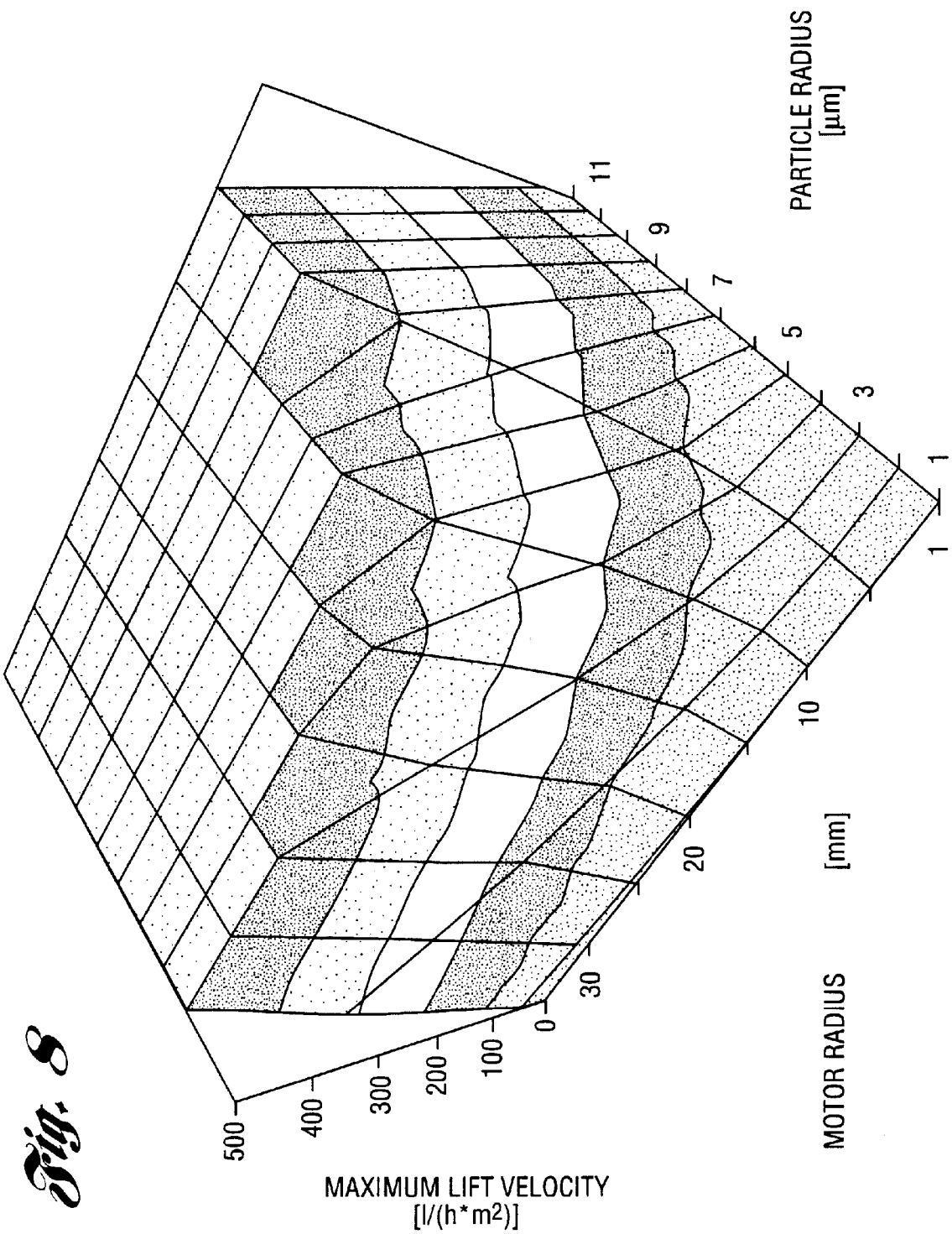
FIG. 8 is a representation of the limit flow rate according to the theory of the "hydrodynamic lift effect" in a preferred arrangement of the filtration apparatus.

FIG. 8 shows calculated limit flow rates for the experimental implementation of the filtration apparatus according to the theory of the "lift force" effect, as a function of the rotor radius and the particle radius.

Calculation statements: $V_{lift}=a^3 * V_w^2 * 0.095/v$ $Y_w=T_w/\eta$; wherein $T_w=1.81*\rho* v^{0.5}* (K*\omega)^{1.5}* r$ wherein a=particle radius, $Y_w$=wall shear rate, v=kinetic viscosity, η=dynamic viscosity, ρ=density, to ω=angular velocity, K=coefficient of friction.

Parameters:

speed of rotation 900 rev/min (ω=94.25 m/s)

density 1000 kg/m³ dynamic viscosity 1.36 mPas

K=0.4

The calculation Example shows that starting from a particle radius >3 μm, as is typical for animal cell cultures, a limit flow rate of >100 l/hm² can be obtained for most of the filter surface (>90% when r>9 mm, where A=f(r²)).

Figure 9:
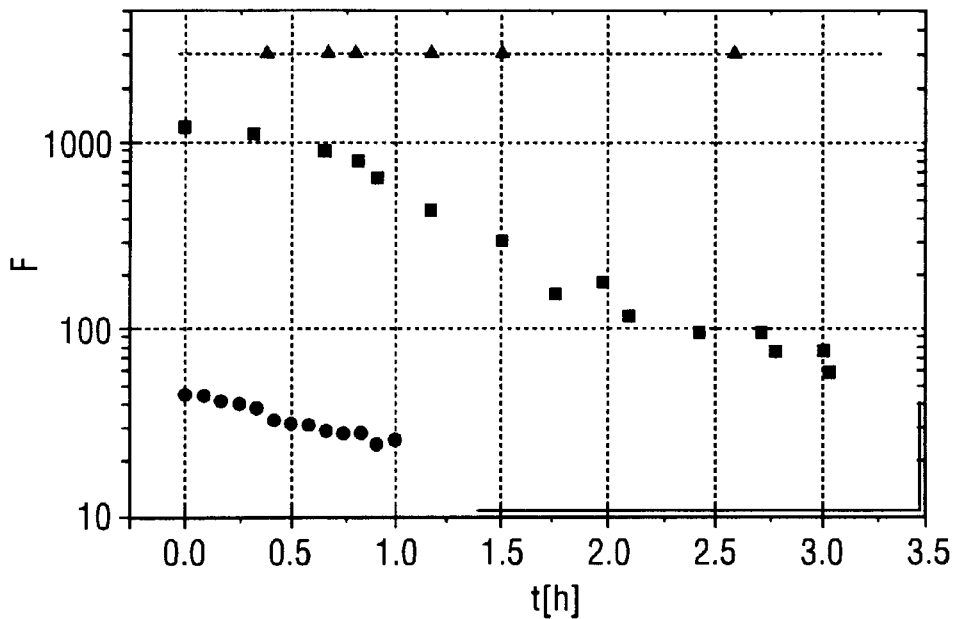
FIG. 9 shows a comparison of the performance of the apparatus according to the invention with that of conventional systems.

FIG. 9 shows a comparison of the performance of the dynamic microfiltration apparatus according to the invention with that of conventional systems. The measurements for the apparatus according to the invention are indicated by small triangles, those for a BIOPEM unit by small rectangles, and those for a conventional cross-flow unit by solid black circles (also in FIG. 10). All three apparatuses work with a wall shear stress of 3 N/m². The pressure-normalized flow rate in units $l·h^{-1}·m^{-2}·bar^{-1}$ is plotted against time t in hours. It should be noted that the pressure-normalized flow rate is represented logarithmically. The superiority of the apparatus according to the invention is clearly recognisable, exhibiting constant behaviour, that is to say no drop in performance, over 3.5 hours. In other words, the filtration flow rate through the filter shows no abatement after 3.5 hours. By contrast, it can clearly be seen that both the BIOPEM filtration unit and the known cross-flow unit show an exponential drop. For example, after 3 hours' service life the BIOPEM unit exhibits less than 10% of its original performance, whilst, as a result of clogging and fouling, the cross-flow unit exhibits only a very low rate of flow through the filter after only one hour.

Figure 10:
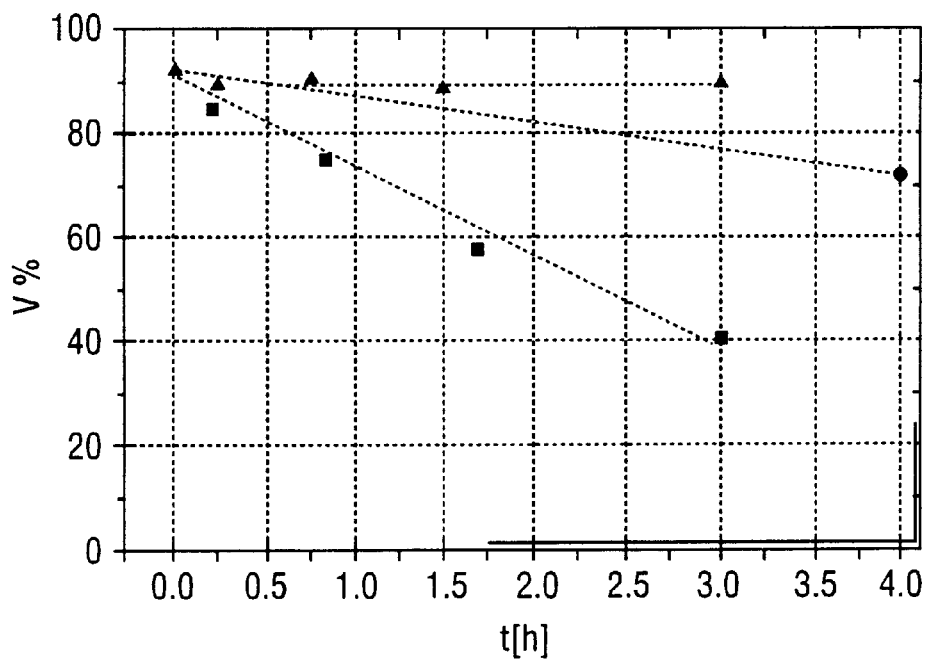
FIG. 10 shows a comparison of the cell vitality of the apparatus according to the invention with the vitality of conventional systems, with the same wall shear stress.

A similar picture is revealed by the comparison of performance in FIG. 10. FIG. 10 shows the vitality in % plotted against time t in hours. Here, also, it can be seen that the vitality in the apparatus according to the invention exhibits a constant curve and shows no drop after 3 hours' operating time. By contrast, the vitality in the cross-flow unit falls from 90 to 70% in 4 hours whilst, with the BIOPEM filtration apparatus, only 40% of the cells exhibit vitality after 3 hours.

Also, in order to achieve a stable filtration performance and also an adequate service life in conventional perfusion systems, low flow rates must be selected. That necessitates the use of large membrane surfaces, which is a main cost factor in conventional membrane processes. Table 1 shows the obtainable stable flow rate values for known filtration apparatuses and for the filtration apparatus according to the invention.

TABLE 1

|  | Cross-flow unit (Prostak, Millipore) | Internal membrane perfusion module | Described apparatus according to the invention |
| --- | --- | --- | --- |
| Flow rate [l * h$^{-1}$ * m$^{-2}$] | 2–6 | 2–10 | 30–50 |

Figure 11A:
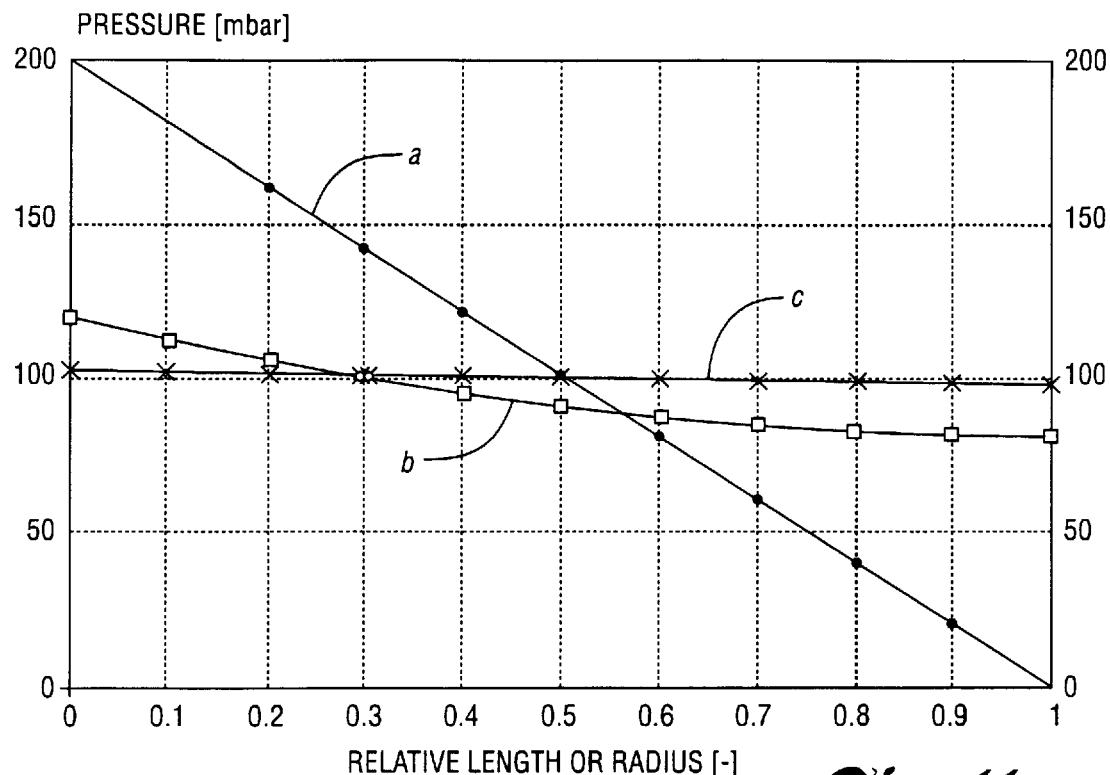
FIGS. 11A and 11B show a comparison of the pressure and flow curves over the filter surface for a conventional tangential flow module (hollow fibres) with those for the filtration apparatus according to the invention.
Figure 11B:
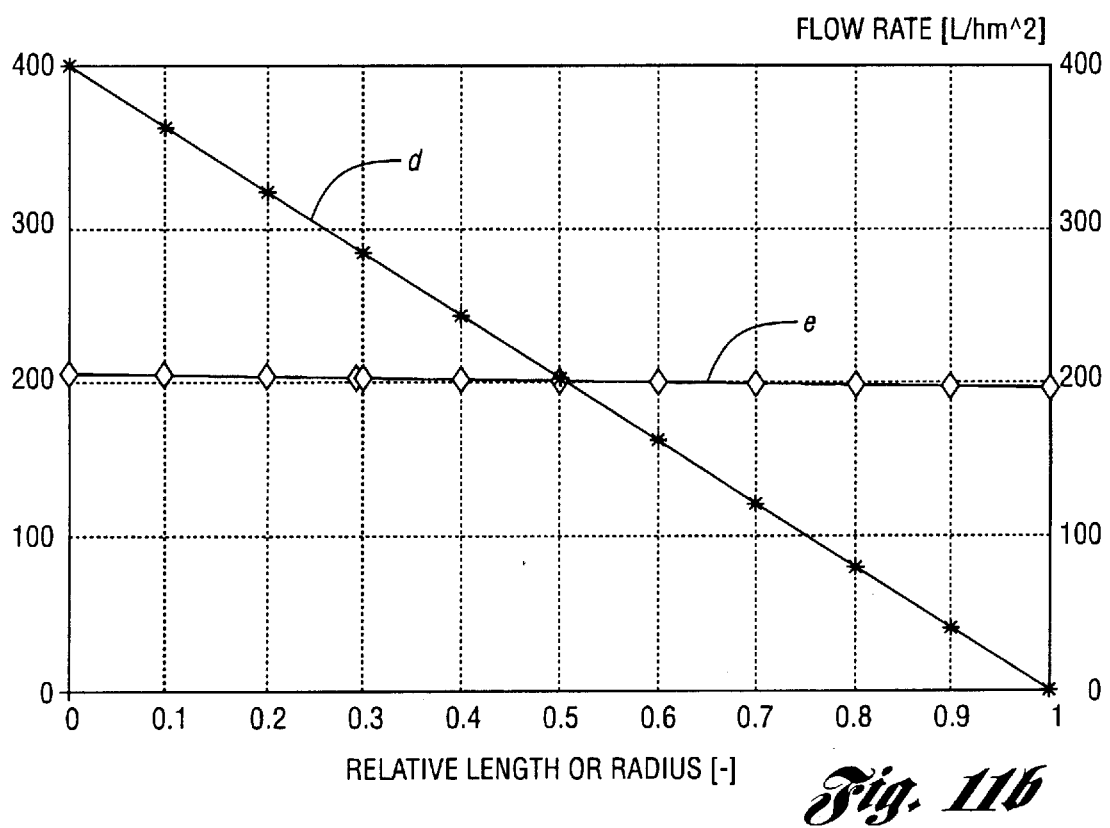

FIGS. 11A and 11B show the pressure and flow curves for water over the characteristic length of the filter surface in a comparison of a conventional tangential flow module (hollow fibres) with the filtration apparatus according to the invention.

Calculation statements:

$$\Delta P = \lambda * 0.5 * \rho * w^2 * L/d_i \text{ (hollow fibres)} \quad (1)$$

wherein $\lambda = 64/Re$ (laminar) and $\lambda = 0.3164 * Re^{-0.25}$ (turbulent)

$$\Delta P = \omega^2 * r^2 * \rho = w^2 * \rho \text{(rotation filter)} \quad (2)$$

The flow rate for both systems is calculated as flow rate=Pm * TMP$_{eff}$, wherein Pm=2000 L/hm$^2$bar and TMP$_{eff}$=TMP$_{average}$ +/−$\Delta P$ (TMP=transmembrane pressure).

Boundary conditions:

Identical constant flow speed or maximum circumferential speed, TMP$_{average}$=0.1 bar;

Hollow fibres: L=30 cm, d$_i$=1 mm, A=700 cm$^2$=75 fibres, w=2 m/s, Re=2000 (lam);

Rotary module: r=15 cm, A=700 cm$^2$, W$_{max}$=2 m/s, $\omega$=13.33.

FIG. 11A:

Pressure curve for (a) hollow fibre module over the relative length in mbar. The average TMP of 0.1 bar is obtained at L/2 (linear pressure loss gradient)

Pressure curve for (b) rotary module (centrifugal pressure nominal) over the relative length (radius). The average TMP is obtained at L=0.293 (1−L/2)

Actual pressure curve for (c) rotary module over the relative length.

The Example shows that, unlike the hollow fibre module, the rotary module has a virtually constant effective pressure prevailing over the filter surface. For scaling-up, there is a further advantage in that when w=$\omega$* r=constant, $\Delta P$ remains constant, in contrast to a tangential flow module in which $\Delta P$ increases with the length.

FIG. 11B:

Flow curve for (d) hollow fibre module and (e) rotary module over the relative length in L/hm$^2$. Starting from the virtually constant effective pressure over the membrane, for the rotary module there is also a virtually constant flow over the total cross-section of the membrane and thus a uniform flow through the filter matrix.

Figure 12:
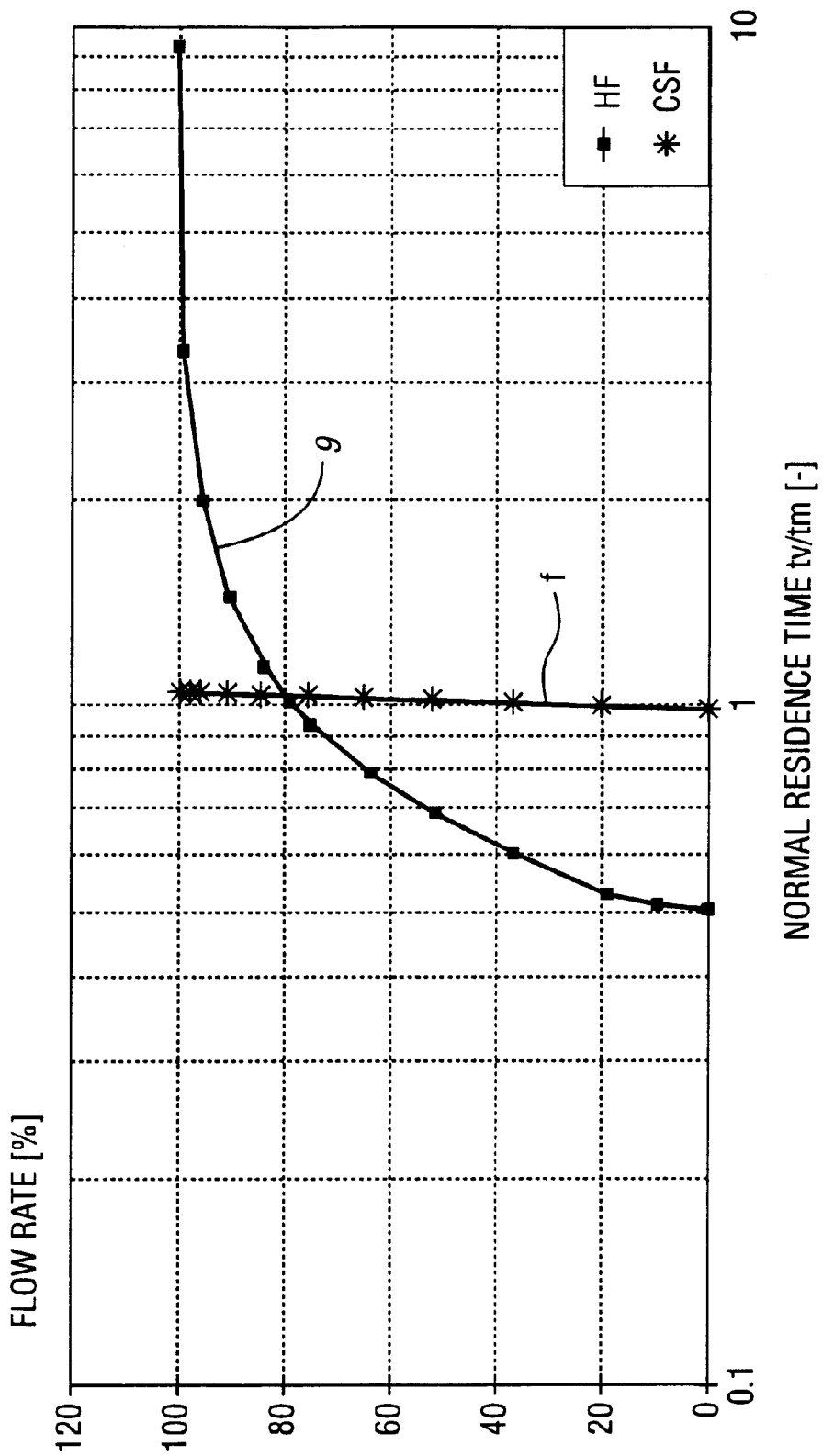
FIG. 12 is a comparison of the residence time distribution for the flow through the filter means for a hollow fibre module with that of the apparatus according to the invention.

FIG. 12 shows a comparison of the residence time distribution for the flow through the filter means for a hollow fibre module (f) and for the module (g) according to the invention. Parameters and conditions are as in FIG. 10. Application: relative surface area-related flow proportion (%) vs. normalized residence time. (a) hollow fibre module, (b) rotary module. Definitions: flow rate (%)=local flow over the membrane length (see FIG. 9)/average flow; normalized residence time=flow-related residence time (t$_v$)/average residence time (t$_m$); t$_v$=filter means (membrane) thickness ($\delta$)/flow; t$_m$=($\delta$)/average flow.

Assumptions: average flow=Pm*TMP=200 l/hm$^2$=5.56 * 10$^{-5}$ m/s; $\delta$=200 µm.

The Example shows that in the rotary module, by virtue of the uniform pressure distribution, a uniform flow is produced through the filter means, with a correspondingly narrow residence time distribution. That ensures that most of the available filter matrix can be utilised, which is especially important when the filter matrix is used actively to enrich a dissolved substance. In contrast thereto, the Example shows that in a conventional tangential flow filter, such as the hollow fibre module, a broad residence time distribution occurs as a result of the longitudinal pressure loss, which, for example in chromatography-analogous operation, results in premature breakthrough, associated with a correspondingly reduced utilisation of the capacity of the filter matrix; if a typical breakthrough limiting value of c/c$_o$=10% is taken as a basis, there is in that case only 52% utilisation of the capacity of the matrix, compared with >98% in the case of the rotary filter. In addition to the improved capacity utilisation—owing to the narrower residence time distribution—improved concentration in the elution of the bound product is to be expected when a rotary filter is used.

Figure 13:
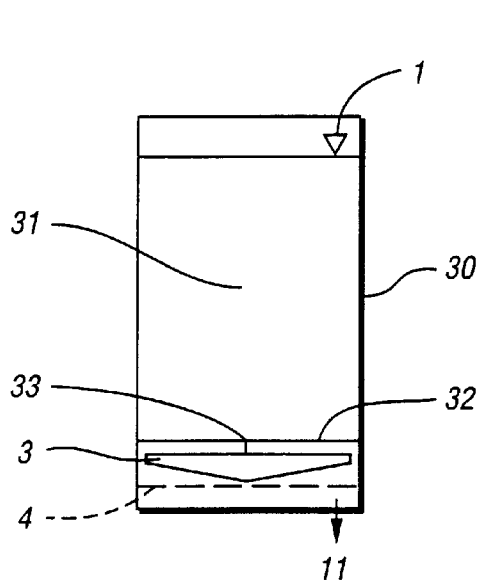
FIG. 13 shows a stirring cell having a conical rotor for batchwise filtration.

FIG. 13 shows a stirring cell having a conical rotor 3 for batchwise filtration. The stirring cell comprises a cylindrical housing 30 having a conical rotor 3 which is arranged in the housing 30 above the planar filter means 4. The suspension to be clarified is supplied 1 into the free space 31 of the stirring cell 30 above the rotor 3. There is arranged in the stirring cell 30 a mounting device 32 for mounting the axle 33 of the rotor 3. The filtrate 11 is removed from the stirring cell 30 in the axial direction whilst the retentate flows back into the space 31 above the rotor 3. Both the apparatus according to FIG. 2 and also the apparatus according to FIG. 3 (double-membrane stirring cell and stirring cell having a conical rotor) may be driven by means of a simple laboratory magnetic stirrer, magnet cores being embedded in the rotor.

Figure 14:
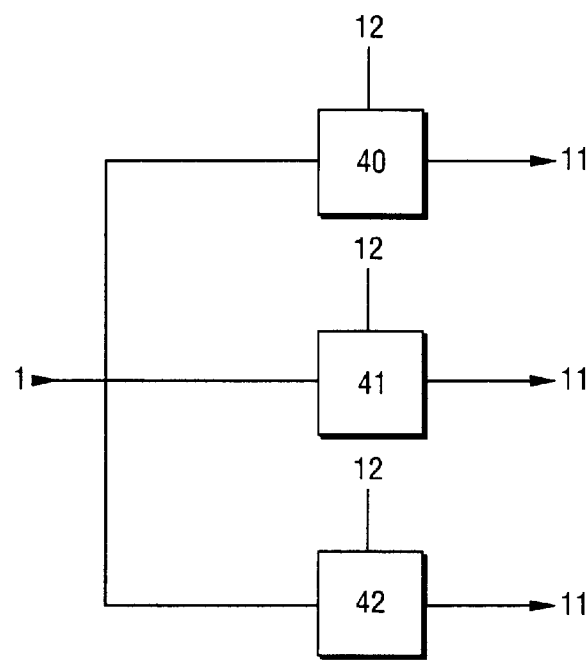
FIG. 14 shows an arrangement in parallel of a plurality of apparatuses according to the invention.

FIG. 14 shows the parallel connection of a plurality of (in this case three) filter apparatuses 40, 41 and 42, each filter apparatus 40, 41 and 42 being supplied at the input side with the supply flow 1 of the solution or suspension to be filtered. The filtrate 11 and the retentate 12 are removed in parallel from the filter apparatuses 40, 41 and 42. As a result of such a parallel connection, the total membrane surface of the system is advantageously increased, as a result of which a higher filtration performance is obtained. As a result of an appropriate arrangement of the filtration apparatuses 40, 41 and 42 in a type of multi-stack construction, it is also possible, for example, for the rotors (not shown) of the filtration apparatuses 40, 41 and 42 to be driven by a common drive. In addition, the parallel-connected filtration apparatus may be arranged, for example, in a common housing in order to reduce the construction costs by means of a modular construction.

Figure 15:
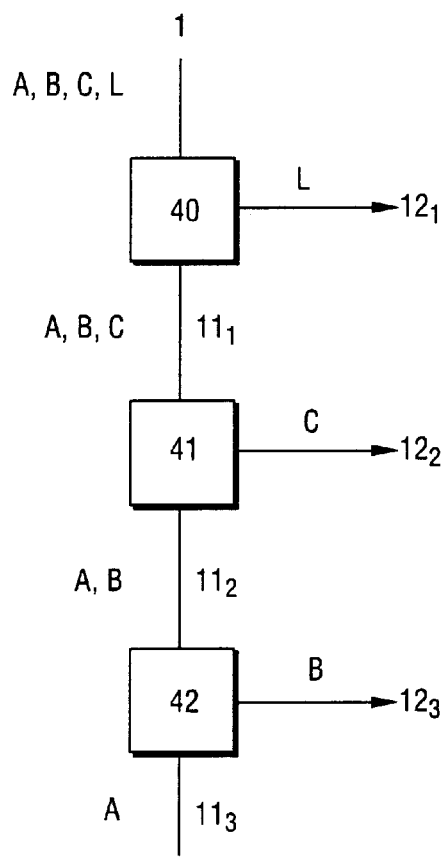
FIG. 15 shows an arrangement in series of a plurality of apparatuses according to the invention.

FIG. 15 shows an arrangement in series of a plurality of filtration apparatuses 40, 41 and 42, the supply flow 1 being supplied to the first filtration device 40. The resulting filtrate 11$_1$ of the first step is used as supply flow to the second filtration apparatus 41. Correspondingly, the filtrate 11$_2$ of the second step of the filtration apparatus 41 is used as input to the third filtration apparatus 42, which yields a filtrate 11$_3$ of the third step. The corresponding filtration apparatuses 40, 41 and 42 each yield a retentate 12$_1$, 12$_2$ and 12$_3$. Such arrangements in series of a plurality of filtration apparatuses are valuable, for example, if each filtration apparatus 40, 41 and 42 is fitted with a special filter means that is different from the others. Accordingly, when, for example, the supply flow contains components A, B and C and residues L, a step-wise filtration can be carried out in such a manner that the filtrate $11_1$ of the first step is clarified and contains components A, B and C, filtrate $11_2$ of the second step contains only components A and B, and filtrate $11_3$ of the third step contains only component A. Accordingly, the retentate $12_3$ of the third step contains only component B, and the retentate $12_2$ of the second step accordingly contains only component C, whilst the retentate of the first step contains the residues L. As a result, the three-step Example can achieve complete separation of the mixture A, B, C and L into pure components A, B and C.

List of Reference Numerals

1—supply flow
2—gap
3—rotor
4—filter means
5—body
6—conical section
7—tip
8—axis of symmetry
9—filter surface
10—through-flow direction
11—filtrate
$11_u$—filtrate
$11_f$—filtrate
$11_1$—filtrate
$11_2$—filtrate
$11_3$—filtrate
12—retentate
$12_u$—retentate
$12_f$—retentate
$12_1$—retentate
$12_2$—retentate
$12_3$—retentate
13—housing
14—upper conical section
15—lower conical section
16—filter means
17—filter means
18—upper cover
19—lower cover
20—upper filtrate space
21—lower filtrate space
22—upper support
23—lower support
24—upper cover
25—lower cover
26—upper bearing
27—lower bearing
28—axle
30—stirring cell housing
31—stirring cell space
32—mounting device
40—filtration apparatus
41—filtration apparatus
42—filtration apparatus S—maximum gap width
$S_f$—distance between the tip of the cone and the filter surface
r—radius
V—vitality
F—pressure-normalized flow rate
A—components
B—components
C—components
L—residues
m—affinity membrane
t—separating layer/membrane
a—active layer/membrane
P—packing
n—number

What is claimed is:

1. A filtration apparatus for separating and/or enriching dissolved substances from a suspension, said apparatus comprising:
a housing accommodating at least one rotor and at least one filter device;
said rotor comprising a rotationally symmetrical conical rotor having a conical section whose apex is directed towards one of said at least one filter device, the cone angle of said conical section being from 3° to 4°, such that a virtually homogenous shear field and a virtually constant pressure gradient are produced across an in-flow section of said filter device;
said filter device comprising a plurality of layers of surface modified membranes or comprising a filter membrane followed by a chromatographic column on the filtrate side of the filter membrane,
wherein the ratio s/r of a maximum gap width s between the filter device surface nearest said rotor and said rotor, to the maximum radius r of said rotor, is less than 0.2.

2. Apparatus according to claim 1, wherein the filter device consists of a plurality of layers that have different functionalities.

3. A filtration apparatus, comprising:
a housing accommodating a rotationally symmetric rotor having a radius r and a filter device comprising at least one filter membrane, said filter device separated from said rotor by a distance s, the distance s increasing with increasing r, such that the ratio s/r determined from the value of s at the maximum radius r of said rotor is less than 0.2, such that a virtually homogenous pressure gradient is produced across an in-flow section of said filter, wherein said rotationally symmetric rotor is selected from the group consisting of a conical rotor having sloping sides and having an apex directed toward said filter device, and a truncated conical rotor having sloping sides and having a truncated apex, said truncated apex directed toward said filter device, said apparatus having a cone angle defined as the included angle between the sloping sides of said rotationally symmetric rotor and said filter device in a radial direction away from the center of rotational symmetry of said rotor about 3° to about 4°.

4. The apparatus of claim 3, wherein said filter membrane is a planar membrane.

5. The device of claim 3, further comprising a chromatographic column downstream from said filter device.

* * * * *